United States Patent
Melki

(10) Patent No.: US 9,561,137 B2
(45) Date of Patent: Feb. 7, 2017

(54) MALE HYGIENE ARTICLE

(71) Applicant: Prevent Hygiene Products AB, Sodertalje (SE)

(72) Inventor: Vilyam Melki, Upplands Vaesby (SE)

(73) Assignee: PREVENT HYGIENE PRODUCTS AB, Sodertalje (SE)

( * ) Notice: Subject to any disclaimer, the term of this patent is extended or adjusted under 35 U.S.C. 154(b) by 243 days.

(21) Appl. No.: 14/359,678

(22) PCT Filed: Nov. 12, 2012

(86) PCT No.: PCT/SE2012/051228
§ 371 (c)(1),
(2) Date: May 21, 2014

(87) PCT Pub. No.: WO2013/081526
PCT Pub. Date: Jun. 6, 2013

(65) Prior Publication Data
US 2014/0343521 A1  Nov. 20, 2014

(30) Foreign Application Priority Data
Nov. 28, 2011  (SE) ........................ 1151131

(51) Int. Cl.
A61F 13/471  (2006.01)
A61F 13/474  (2006.01)
(Continued)

(52) U.S. Cl.
CPC ............ *A61F 13/471* (2013.01); *A61F 5/453* (2013.01); *A61F 13/148* (2013.01);
(Continued)

(58) Field of Classification Search
CPC .. A61F 13/471; A61F 13/476; A61F 13/4915; A61F 13/5605; A61F 13/82; A61F 5/453; A61F 13/474
(Continued)

(56) References Cited

U.S. PATENT DOCUMENTS 5,094,234 A  3/1992  Searcy
6,680,421 B1  1/2004  Ravo
(Continued)

FOREIGN PATENT DOCUMENTS

EP  0114560 A2  8/1984
WO  WO-9416655 A1  8/1994
WO  WO-2009141640 A1  11/2009

OTHER PUBLICATIONS

International Search Report issued Mar. 22, 2013 in PCT/SE2012/051228 filed on Nov. 11, 2012.
(Continued)

*Primary Examiner* — Lynne Anderson
*Assistant Examiner* — Kathryn E Ditmer
(74) *Attorney, Agent, or Firm* — Harness, Dickey & Pierce, P.L.C.

(57) ABSTRACT

A one-piece hygiene article is disclosed for use by a male to absorb moisture in the crotch region, wherein the hygiene article includes an absorbent material. The hygiene article further includes a first absorbing portion, having a V-shape for receiving the genitals of the male. The legs of the V-shape of the first absorbing portion are arranged for being provided along the groin and on either side of the genitals of the male. A second absorbing portion extends from the base of the V-shape of the first absorbing portion and has an elongated shape, wherein the second absorbing portion is arranged for being provided between the buttocks of the male. The hygiene article further includes at least one
(Continued)

weakening line for a length adjustment of the hygiene article, and an adhesive material for adhering the hygiene article to the crotch of the male.

20 Claims, 3 Drawing Sheets

(51) Int. Cl.
    *A61F 13/84*     (2006.01)
    *A61F 13/491*     (2006.01)
    *A61F 13/82*     (2006.01)
    *A61F 13/14*     (2006.01)
    *A61F 5/453*     (2006.01)
    *A61F 13/56*     (2006.01)
    *A61F 13/00*     (2006.01)
    *A61F 13/15*     (2006.01)

(52) U.S. Cl.
    CPC ........ *A61F 13/474* (2013.01); *A61F 13/4915* (2013.01); *A61F 13/5605* (2013.01); *A61F 13/82* (2013.01); *A61F 13/8405* (2013.01); *A61F 2013/00395* (2013.01); *A61F 2013/15097* (2013.01); *A61F 2013/8408* (2013.01)

(58) Field of Classification Search
    USPC ............................................ 604/359, 385.03
    See application file for complete search history.

(56) References Cited

U.S. PATENT DOCUMENTS

| | | |
|---|---|---|
| 6,997,915 B2 | 2/2006 | Gell et al. |
| 2002/0193766 A1 | 12/2002 | Gell et al. |
| 2008/0039760 A1 | 2/2008 | Lesko |

OTHER PUBLICATIONS

Written Opinion issued Mar. 22, 2013 in PCT/SE2012/051228 filed on Nov. 11, 2012.
Extended European Search Report dated Jun. 9, 2015.

MALE HYGIENE ARTICLE

This application is the national phase under 35 U.S.C. §371 of PCT International Application No. PCT/SE2012/051228 which has an International filing date of Nov. 12, 2012, which designated the United States of America, and which claims priority to Swedish patent application number SE 1151131-8filed Nov. 28, 2011, the entire contents of each of which are hereby incorporated herein by reference.

FIELD OF THE INVENTION

The present invention relates to a male hygiene article for medicinal, hygiene and/or aesthetic purposes.

BACKGROUND OF THE INVENTION

Males of any age may be affected by irritations and/or infections in or around the crotch, wherein these irritations may appear as itching, burning sensations and/or pain in the groin area, (uro)genital area, thigh skin folds, anus (perianal area) and/or between the buttocks (intergluteal area). Affected areas may appear on the thigh and/or scrotum side as red, tanned, or brown areas, with flaking, rippling, peeling, or cracking skin, wherein the condition may result in a general discomfort or pain. Moreover, dermal body fluid discharges may appear in the crotch region due to infections.

The crotch region may often be exposed to a warm, damp environment from tight, sweaty clothing such as underwear and/or jock straps. This may contribute to the cultivation of fungus, which may cause crotch itches. To prevent the occurrence of crotch irritations and/or infections, it has been suggested to keep the crotch region clean and dry by e.g. drying off thoroughly after bathing, putting on dry clothing immediately after swimming or perspiring, not sharing clothing or towels with others, showering immediately after athletic activities, wearing loose cotton underwear, avoiding tight-fitting clothing and/or using antifungal, antibacterial powders and/or ointments in the crotch region.

However, the above-mentioned actions to prevent e.g. crotch itch and/or discomforts in the crotch region may be tedious and inconvenient. Therefore, there is a wish to more conveniently inhibit the occurrence of crotch itches, irritations and/or infections.

In patent document U.S. Pat. No. 5,094,234, there is provided a soft goods appliance for eliminating crotch itch. The appliance comprises en elastic waistband from which a center strap extends downward from the rear and towards the front. The front distal end of the center strap forms a concave pouch, intervening between the scrotum and penis, wherein vertically oriented side straps on the front of the appliance secure the pouch to the waistband.

Patent document U.S. Pat. No. 6,680,421 shows a protective inguinal perineal element for male and female patients, wherein the element is to be worn by the patient under a piece of underwear. The element comprises an absorbent cushion, and the element is arranged to absorb liquids from transpiration, exudation, and secretions present in the inguinal and perineal areas of the patient.

However, there are problems related to these appliances, as the constructions of the appliances are inconvenient, troublesome and obstructive for the user.

SUMMARY OF THE INVENTION

It is an object of the present invention to mitigate the above problems and to provide a more convenient article for medicinal, hygiene and/or aesthetic purposes related to the male crotch region.

This and other objects are achieved by providing an article having the features defined in the independent claim. Preferred embodiments are defined in the dependent claims.

Hence, according to a first aspect of the present invention, there is provided a one-piece hygiene article for use by a male to absorb moisture in the crotch region, wherein the hygiene article comprises an absorbent material. The hygiene article further comprises a first absorbing portion, having a "V"-shape for receiving the genitals of the male. The legs of the "V"-shape of the first absorbing portion are arranged for being provided along the groin and on either side of the genitals of the male. The hygiene article further comprises a second absorbing portion which extends from the base of the "V"-shape of the first absorbing portion and has an elongated shape, wherein the second absorbing portion is arranged for being provided between the buttocks of the male. The hygiene article further comprises at least one weakening line arranged for allowing an adjustment of the length of the hygiene article. Moreover, an adhesive material is provided on the hygiene article for adhering the hygiene article to the crotch of the male.

Thus, the present invention is based on the idea of providing a one-piece hygiene article for men for absorbing moisture in the urogenital, perianal and/or intergluteal areas/regions. The one-piece hygiene article, to be applied in the crotch region, forms a "Y-shape", wherein the first absorbing portion constitutes the portion of the "V"-shape of the hygiene article, whereas the second absorbing portion constitutes the portion of the "I"-shape of the hygiene article.

The base of the "V"-shape of the first absorbing portion is arranged to be provided under/behind the genitals (i.e. scrotum and penis) of the male, whereas the legs of the "V"-shape are arranged to extend from under/behind the genitals and along the groin and on either side of the genitals. The first absorbing portion is hereby adapted to the male crotch/groin anatomy, wherein the legs of the "V"-shape are adapted to be arranged on either side of the male genitals along the groin. The second absorbing portion of the hygiene article, constituting the "I"-shape of the hygiene article, is arranged to extend from under/behind the genitals and between the buttocks of the male. The second absorbing portion is hereby adapted to the male intergluteal anatomy. Furthermore, the at least one weakening line allows an adjustment of the length of the hygiene article, and the adhesive material adheres the hygiene article to the crotch of the male.

The one-piece article for moisture absorption, as disclosed in the present invention, is advantageous as it is easily and conveniently applied by the user. Furthermore, the article is convenient and comfortable to wear by a user, as the hygiene article is adaptable in size (length) by the at least one weakening line. Moreover, the provision of an adhesive material on the hygiene article for crotch adhesion even further contributes to a convenient and comfortable wear. In contrast, prior art appliances/articles/arrangements are often inconvenient, troublesome and/or obstructive at application and/or during wear. This is especially the case for appliances wherein two or more pieces, e.g. bands, straps, belts and/or girdles, have to be attached by the user. Furthermore, prior art appliances often have a one-size construction which cannot be adapted in size and/or that the appliances are not able to stay in place during use. Appliances or arrangements of this kind lead to a cumbersome and awkward operation, and may furthermore be uncomfortable for the user. Hence, the one-piece moisture-absorbing article of the present invention is therefore advantageous in that it is easily and conveniently applied to the crotch region of the male user, and that the article is more easily and conveniently worn by the user.

The present invention is further advantageous in that the moisture-absorbing hygiene article may prevent and/or treat irritations, eczematous rashes, skin eruptions and/or general discomforts in the urogenital, perianal and/or intergluteal regions. Hence, the prophylactic aspect of the hygiene article may prevent the occurrence of e.g. itches, infections, eczema and/or haemorrhoid-related ailments in the mentioned regions.

Another advantage of the present invention is that the hygiene article may prevent and/or treat infections in the urogenital, perianal and/or intergluteal regions, wherein these infections may be caused by infectious agents such as virus, bacteria, and/or fungus. Hence, in a medical aspect, the hygiene article may prevent diseases caused by these infectious agents.

Another advantage of the present invention is that the hygiene article may keep any ointments, liniments or the like, which are applied in the crotch region, in place. For example, after applying an ointment to the crotch region, the hygiene article may be applied to (at least partially) cover the ointment. The hygiene article may thereby avoid any smearing out of ointments applied in the crotch region and/or prevent a smudging of the underwear.

Furthermore, as the hygiene article is arranged for absorbing moisture from the urogenital, perianal and/or intergluteal regions, the hygiene article also provides advantages in a hygienic aspect. The moisture-absorbing material of the hygiene article may reduce smells from the mentioned crotch regions, thereby increasing the health, comfort, and the sense of freshness, cleanliness and well-being of the user.

Another advantage of the present invention is that the hygiene article may at least partly separate the male genitals, the crotch and/or the buttocks such that a skin contact between the penis/scrotum and the crotch and/or the skin contact between the buttocks is (at least partly) impeded. By avoiding skin contact between the organs/body parts in the crotch region, the hygiene article may relieve irritations, rashes and/or discomforts in the urogenital, perianal and/or intergluteal regions.

By its relative simplicity as a one-piece article, compared to appliances comprising two or more pieces, the hygiene article further provides the advantage of being simple and inexpensive to fabricate. Furthermore, as the hygiene article is soft and supple, it is convenient to apply in the crotch region (i.e. at the genitals and between the buttocks), comfortable, and easily portable. The lithe hygiene article of the present invention may provide a form which adapts to the anatomy of the user, further contributing to the comfort of the user. Moreover, when not in use, the hygiene article is easily portable, e.g. in a bag.

Another advantage of the present invention is that the hygiene article may be disposable, i.e. it may be of a throw-away type. Hence, after use, the hygiene article may be rejected, and a new hygiene article may be applied. Alternatively, the hygiene article may be washed by hand or in a washing machine, such that the hygiene article may be reused.

Another advantage of the present invention is that the hygiene article may emphasize the genitals of the male, i.e. the penis and/or scrotum, when applied in the crotch region as described. In other words, the "V"-shape of the first absorbing portion of the hygiene article may support, lift and/or push up the genitals. By this, a more aesthetic profile with respect to the body silhouette may be provided.

Another advantage of the present invention is that the hygiene article, due to its properties of being lithe, light and flexible, may stay in place when applied to the region of the genitals and between the buttocks of the user, even though the user may perform physical activities and/or exercises such as running, cycling, playing football, etc.

By the term "moisture", it is here meant (predominantly) sweat and/or dermal body fluid discharges. The moisture may occur in the crotch region due to e.g. physical activity, nervousness, heat, infections, etc. Other body liquids such as e.g. traces of urine, semen and/or blood may however also be comprised within the meaning of the term.

By the term "receiving", it is here meant that when applying the hygiene article to the crotch region, the male genitals (i.e. penis and scrotum) are provided within the "V"-shape of the first absorbing portion, such that the base of the "V"-shape is provided under/behind the root of the genitals.

The hygiene article comprises an absorbent material, which may be substantially any material which has high absorption properties. Furthermore, the hygiene article may comprise hydrophobic materials for the purpose of retaining moisture, absorbed by the absorbent material, within the article. Furthermore, the hygiene article may comprise e.g. textiles for reasons of hygiene article structure and/or for a re-utilization of the hygiene article, by means of washing.

It will be appreciated that the second absorbing portion of the hygiene article, arranged for being provided between the buttocks, may further be arranged to extend beyond the intergluteal area/region. In other words, an (end) portion of the second absorbing portion may project/extend from between the buttocks after applying the hygiene article. By this, the user may grip the (end) portion behind his back and conveniently tighten the fit of the hygiene article.

The hygiene article comprises at least one weakening line arranged for allowing an adjustment of the length of the hygiene article. By the term "weakening line", it is here meant substantially any kind of line of/in the material which facilitates a tearing/separation of the material. The at least one weakening line may be provided substantially perpendicular to the longitudinal direction of the elongated hygiene article, and the length of the hygiene article may hereby be adjusted by tearing off at least one portion of the article at the weakening line(s). The hygiene article hereby provides the advantage that it may be adapted/adjusted to the individual size of the urogenital, perianal and/or intergluteal region(s) of the user and/or to the individually preferred use of the hygiene article. For example, a user having a relatively small scrotum, penis and/or intergluteal passage may want to adjust/shorten the length of the hygiene article. The length of the hygiene article may also be shortened if the user prefers a tight fit of the hygiene article. Alternatively, a user having a relatively large scrotum, penis and/or intergluteal passage may prefer only a small adjustment the length of the hygiene article, or no adjustment at all. It will be appreciated that appliances in the prior art often have a one-size construction which cannot be individually adapted to the user. This may not only deteriorate the function of the appliance, but may also negatively influence the comfort of the user when wearing the appliance. In the present invention, on the other hand, the user may adjust the length of the hygiene article, and the at least one weakening line of the hygiene article provides a simple and intuitive way of individual user size adjustment by removal of at least one portion of the hygiene article at the weakening line(s).

The one-piece hygiene article is provided with an adhesive material for adhering the hygiene article to the crotch of the male. By the term "adhesive material", it is here meant any kind of chemical adhesive which may adhere to the hygiene article to skin, such as glue, tissue glue, or the like. The adhesive material applied to the hygiene article is advantageous in that the hygiene article may even more easily stay in place compared to the case when no adhesive material is applied. This may especially be advantageous during any kind of (intense) physical activity or exercise of the user such as running, cycling, weight training, playing football, etc. It will be appreciated that the adhesive material may be provided substantially anywhere on the hygiene article, with the purpose of adhering the hygiene article to the crotch. The present invention is hereby advantageous compared to prior art appliances without any adhesive material, as these appliances are more likely to fall out of place during use. A displacement of the appliance may not only deteriorate the function of the appliance, but may also lead to an uncomfortable wear of the appliance.

The adhesive material further provides the advantage that the hygiene article, adhering to the crotch, may be worn without underwear. It will be appreciated that appliances in the prior art often necessitate that the user wears the appliance with underwear, i.e. that a piece of underwear is required to keep the appliance in place. However, as the material of the underwear may be heat insulating, the user may experience an increase in perspiration in the crotch area during underwear use. In the present invention, on the other hand, the hygiene article may be worn without underwear due to the provision of adhesive material on the article. This is highly advantageous for a user who wants to avoid the use of underwear, e.g. when the user wants to avoid the risk of an increased perspiration and/or when the user wishes to achieve an increased airiness in the crotch region. Furthermore, it will be appreciated that the provision of adhesive material to the hygiene article is adjusted so that enough adhesive material is applied for the purpose of providing a satisfactory adhesion of the hygiene article to the crotch, whereas the amount and/or properties of the adhesive material is adapted such that a removal of the hygiene article after use still is easy and convenient for the user (i.e. that the hygiene article does not become too firmly adhered to the crotch). Moreover, it will be appreciated that an adhesive material of the hygiene article may be applied along a length of the hygiene article which exceeds the length of any portion of the article comprising the at least one weakening line. In other words, after any optional removal of a portion of the hygiene article at the one or more weakening lines, the hygiene article may still be provided with adhesive material for an adhesion to the groin of the user.

According to an embodiment of the present invention, the adhesive material may be provided at end parts of the legs of the first absorbing portion and at an end part of the second absorbing portion. In other words, the adhesive material may be provided to the three end/tip parts of the "Y"-shape of the hygiene article. The present embodiment is advantageous in that the user may easily and conveniently adhere the hygiene article to the crotch, and analogously, remove the hygiene article from the crotch after use. The two end/tip parts of the "V"-shape of the first absorbing portion may be adhered to the groin, i.e. a portion of the abdomen/pelvic region, whereas the end/tip part of the "I"-shape of the second absorbing portion may be adhered to a portion of the crotch beyond the intergluteal area/region, e.g. the lower back/spine.

According to an embodiment of the present invention, the one-piece hygiene article may be provided with attachment means for fastening the hygiene article to a piece of underwear. The attachment means may be substantially any kind of means for attaching the hygiene article to the piece of underwear, such as Velcro® tape, adhesive material, etc. The present embodiment is advantageous in that the fastening of the hygiene article to the piece of underwear to an even higher extent holds the hygiene article in place after being applied to the crotch. The embodiment is especially beneficial when a user performs any kind of physical activity or exercise.

According to an embodiment of the present invention, at least one first segment of the legs of the first absorbing portion may be provided with at least one first weakening line, arranged for allowing an adjustment of the length of the legs of the first absorbing portion by tearing off a portion of the at least one first segment at the first weakening line. The at least one first weakening line may be provided substantially perpendicular to the elongation of the legs of the "V"-shape of the first absorbing portion of the hygiene article such that the length of the legs may be adjusted by tearing off a portion of the at least one first segment of the hygiene article. The present embodiment is advantageous in that the hygiene article may be adapted/adjusted to the individual size of the urogenital, perianal and/or intergluteal regions of the user and/or the individually preferred use of the hygiene article. For example, a user having a relatively small scrotum, penis and/or intergluteal passage may want to adjust/shorten the length of the hygiene article. This may also be the case if the user prefers a tight fit of the hygiene article. Alternatively, a user having a relatively large scrotum, penis and/or intergluteal passage may prefer only a small adjustment the length of the hygiene article, or no adjustment at all. In any case, the at least one weakening line provides a simple and intuitive way of individual user size adjustment by removal of at least one first segment of the hygiene article. It will be appreciated that if an adhesive material is provided at end parts of the legs of the first absorbing portion, according to an embodiment of the present invention, the adhesive material may be applied along a length of the end parts such that after any removal of at least one first segment of the hygiene article, the hygiene article will still provide end parts of the legs of the first absorbing portion provided with adhesive material for adhesion to the groin of the user.

According to an embodiment of the present invention, at least one second segment of the second absorbing portion may be provided with at least one second weakening line, arranged for allowing an adjustment of the length of the second absorbing portion by tearing off a portion of the at least a segment at the second weakening line. The at least one second weakening line may be provided substantially perpendicular to the elongation of the "I"-shape of the second absorbing portion of the hygiene article, such that the length of the second absorbing portion may be adjusted by tearing off a portion of the at least one second segment of the hygiene article. The present embodiment is advantageous in that the hygiene article may be adapted/adjusted to the individual size of the urogenital, perianal and/or intergluteal areas/regions of the user and/or the individually preferred use of the hygiene article. It will be further be appreciated that if an adhesive material is provided at an end part of the second absorbing portion, according to an embodiment of the present invention, the adhesive material may be applied along a length of the end part such that after any removal of at least one second segment of the hygiene article, the hygiene article will still provide an end part of the second absorbing portion which is provided with adhesive material for adhesion to a portion of the crotch beyond the intergluteal area/region, e.g. a portion of the lower back/spine of the user.

According to an embodiment of the present invention, a third weakening line may extend from the base of the "V"-shape of the first absorbing portion and along at least a part of the second absorbing portion, the third weakening line being arranged for allowing an adjustment of the size of the first absorbing portion by tearing apart the at least a part of the second absorbing portion along the third weakening line. The present embodiment is advantageous in that the third weakening line, extending from the base of the "V"-shape of the first absorbing portion and into the "I"-shape of the second absorbing portion, provides the possibility to further adapt the size apportionment between the first and the second absorbing portions. In other words, by tearing along the third weakening line, the first absorbing portion is enlarged (the lengths of the legs of the first absorbing portion are increased), whereas the second absorbing portion thereby is decreased. Hence, the present embodiment is advantageous in that it provides an easy and convenient adjustment of the hygiene article for an even more convenient and/or comfortable fit for the user.

According to an embodiment of the present invention, one or more of the first, second and third weakening lines may be a perforation line, a folding line, a bending line, or a combination thereof. The present embodiment is advantageous in that the exemplifying weakening lines provide an easy and convenient tearing of the hygiene article for individual size adjustment.

According to an embodiment of the present invention, the absorbent material may be made of cellulose, cellulose fluff, wood fluff, cotton, or a combination thereof. An advantage with the absorbent materials proposed for the hygiene article is that they may absorb and retain extremely large amounts of a moisture relative to the mass of the hygiene article material used. A further advantage of the absorbent materials proposed in the present embodiment is that the materials are soft and pliable, providing comfort for the user. Furthermore, the mentioned absorbent materials provide the ability of the hygiene article to be easily folded and transported, when not in use. It will be appreciated that the mentioned absorbing materials are exemplifying, and that the absorbent material may comprise substantially any material, or any combination of material, which is moisture absorbing.

According to an embodiment of the present invention, the hygiene article may further comprise a medicinal agent and/or deodorant. By the term "medicinal agent", it is here meant any medicament for the cure, treatment or prevention of disease. More specifically, the medicinal agent may be a liquid, a gel, an ointment, or the like, such that at least a portion of the hygiene article may be impregnated with the medical agent. By the term "deodorant", it is here meant any substance for eliminating or reducing odor caused by the bacterial breakdown of perspiration. An advantage with the embodiment of the present invention is that the medicinal agent and/or deodorant may further prevent and/or treat irritations, infections, eczematous rashes, eruptions and/or general discomforts in the urogenital, perianal and/or intergluteal areas/regions. A further advantage of the present embodiment is that the medicinal agent and/or deodorant may further inhibit or reduce odor and/or provide a pleasant scent, which may increase the sense of freshness and/or well-being of the user.

According to an embodiment of the present invention, the length of the hygiene article may be within 40-80 cm, such as within 50-70 cm. A relatively long length of the hygiene article may be preferred by a user having a relatively large scrotum, penis and/or intergluteal passage. If the length of the hygiene article is considered by the user to be too long, an adjustment is possible by means of the weakening lines, according to one or more of the previous embodiments, such that one or more parts/portions/segments of the hygiene article may be torn off. Further, the mentioned intervals of the length of the hygiene article may represent a length which is sufficiently short such that the hygiene article may be easily portable, e.g. in a bag.

According to an embodiment of the present invention, the width of the hygiene article may be within 0.5-5 cm, such as within 1-3 cm. By the term "width", it is here meant the width of one leg of the "V"-shape of the first absorbing portion, the width of both legs of the "V"-shape of the first absorbing portion and/or the width of the second absorbing portion. The mentioned intervals of the width of the hygiene article may provide a hygiene article which is sufficiently small in width such that it is supple, conveniently applied and easily portable, still being sufficiently large in width such that the hygiene article is suitable for its purposes, i.e. for absorbing moisture.

According to an embodiment of the present invention, there is provided an underwear garment, comprising a one-piece hygiene article according to any one of the previously described embodiments, wherein the underwear garment further comprises an elastic waistband arranged to surround the torso of the male, wherein the waistband is attached to the legs of the first absorbing portion and to the second absorbing portion so as to define openings for the legs of the male when putting on and wearing the underwear garment. The present embodiment is advantageous in that the elastic waistband, to an even further extent, holds the hygiene article in place, which is especially beneficial when the user performs any kind of physical activity. Furthermore, the underwear garment provides an even more facilitated and convenient application of the hygiene article to the crotch. It will be appreciated that the underwear garment may be provided under any piece of underwear (e.g. boxer shorts, briefs) or, alternatively, be applied by the user without any other piece of underwear. Furthermore, it will be appreciated that substantially all described advantages of the hygiene article also hold for the underwear garment, and it is referred to those parts of the text. Moreover, the underwear garment of the present embodiment has a form which to a much lesser extent covers the skin of a user compared to underwear in the prior art, e.g. briefs and/or boxer shorts. Hence, the underwear garment reduces the risk of an increased perspiration in the crotch region compared to prior art underwear, and may furthermore achieve an increased airiness in the crotch region.

According to an embodiment of the present invention, the width of the hygiene article of the underwear garment may be within 0.5-2 cm, such as within 0.5-1 cm. The present embodiment is advantageous in that the underwear garment is hereby provided as a "string"-type, which due to its reduced size, compared to a wider hygiene article, may become even further convenient and/or comfortable for the user.

Further objectives of, features of, and advantages with, the present invention will become apparent when studying the following detailed disclosure, the drawings and the appended claims. Those skilled in the art will realize that different features of the present invention can be combined to create embodiments other than those described in the following.

BRIEF DESCRIPTION OF THE DRAWINGS

These and other aspects of the present invention will now be described in more detail, with reference to the appended drawings showing a currently preferred embodiment of the invention, wherein.

DETAILED DESCRIPTION OF THE INVENTION

In the following description, the present invention is described with reference to a hygiene article for use by a male to absorb moisture.

Figure 1:
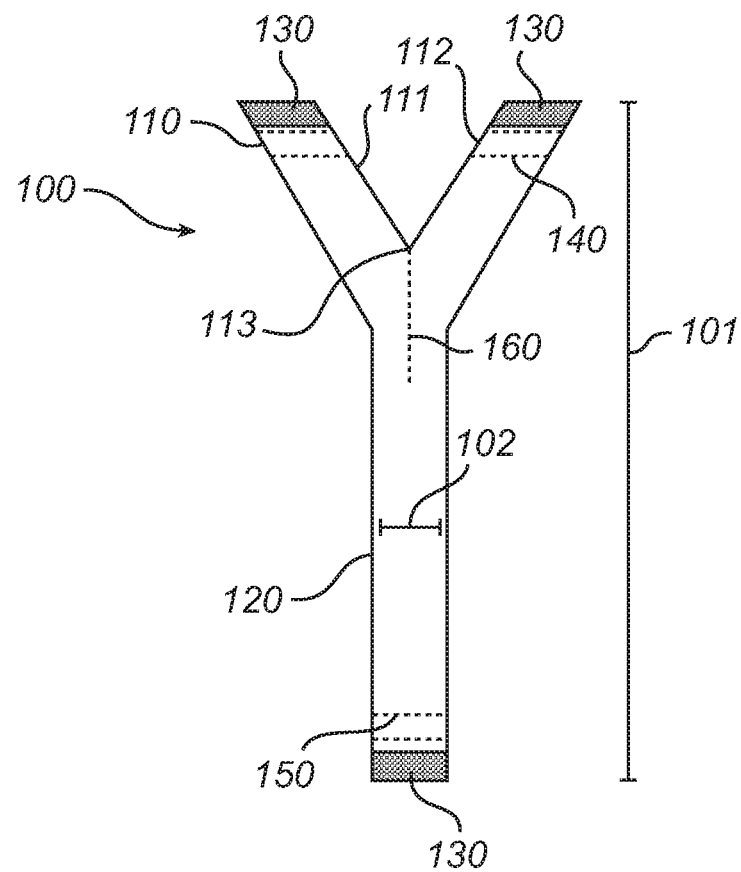
FIG. 1 is a schematic illustration of the hygiene article.

FIG. 1 is a schematic illustration of the hygiene article 100. The length 101 of the hygiene article 100 is approximately 40-80 cm, and the width 102 of the hygiene article 100 is approximately 1-3 cm (it will be appreciated that the hygiene article 100 is not drawn to scale). The thickness of the hygiene article 100 may be smaller than the width 102, yielding a substantially flat or oval shape of the hygiene article 100. Alternatively, the hygiene article 100 may also be provided with a substantially round shape. The hygiene article 100 may comprise substantially any material, or any combination of material, which is moisture absorbing, such as cellulose, cellulose fluff, wood fluff, cotton, or the like, or a combination thereof. The hygiene article 100 may further comprise hydrophobic materials, e.g. for the purpose of retaining moisture within the hygiene article 100.

The hygiene article 100 forms a "Y-shape", wherein the first absorbing portion 110 constitutes the portion of the "V"-shape of the hygiene article 100, and wherein the second absorbing portion 120 constitutes the portion of the "I"-shape of the hygiene article 100.

The "V"-shape of the first absorbing portion 110 comprises legs 111, 112. In other words, the legs 111, 112 project from a base portion of the first absorbing portion 110, whereby the legs 111, 112 form an angle. The angle between the legs 111, 112 may be e.g. 20°-160°, such as 20°-160°, or 45°-135°. The first absorbing portion 110 is arranged for receiving the genitals of the male, wherein the base 113 of the "V"-shape of the first absorbing portion 110 is arranged to be provided under/behind (at the root of) the genitals (i.e. scrotum and penis) of the male when the hygiene article 100 is applied to the crotch of the male. The legs 111 and 112 are arranged to extend from under/behind the genitals and along the groin and on either side of the genitals.

The elongated, second absorbing portion 120 of the hygiene article 100 extends from the base 113 of the first absorbing portion 110. During use of the hygiene article 100, the second absorbing portion 120 is arranged to be provided between the buttocks of the male.

In FIG. 1, an adhesive material 130 is applied to end parts of the legs 111, 112 of the first absorbing portion 110, and to an end part of the second absorbing portion 120, for adhering the hygiene article 100 to the crotch of the male user, e.g. to the groin and to a portion of the lower back/spine, respectively. Although FIG. 1 shows that only the outermost parts of the first and second absorbing portions 110, 120 comprise the adhesive material 130, it will be appreciated that the adhesive material 130 may further be provided along a greater portion/length of the legs 111, 112 and or the second absorbing portion 120. Alternatively, the entire hygiene article 100 may be provided with the adhesive material 130 for adhering the hygiene article 100 to the crotch.

A plurality of first weakening lines 140 (here exemplified as perforation lines) are provided at (end) segments of the legs 111, 112 of the first absorbing portion 110. The plurality of first weakening lines 140, provided in parallel and elongating substantially perpendicular to the elongation of the legs 111, 112, are arranged for allowing an adjustment of the length of the legs 111, 112 by tearing off one or more portions of the segments at the first weakening lines 140. It will be appreciated that the adhesive material 130 may be applied along a length of the legs 111, 112, such that after an (optional) removal/tearing off of one or more segments of the first absorbing portion 110, the first absorbing portion 110 may still provide end parts of the legs 111, 112 provided with adhesive material 130 for adhesion of the hygiene article 100 to the groin of the user.

Analogously, a plurality of second weakening lines 150 (here exemplified as perforation lines) are provided at an (end) segment of the second absorbing portion 120. The plurality of second weakening lines 150, provided in parallel and elongating substantially perpendicular to the elongation of the second absorbing portion 120, are arranged for allowing an adjustment of the length of the second absorbing portion 120 by tearing off one or more portions of the segment at the second weakening lines 150. Further, it will be appreciated that any adhesive material 130 may be applied along a length of the second absorbing portion 120, such that an adhesion of the second absorbing portion 120 to the groin of the user may still be provided, even after an (optional) removal/tearing off of a segment of the second absorbing portion 120.

In FIG. 1, a third weakening line 160 (here exemplified as a perforation line) extends from the base 113 of the "V"-shape of the first absorbing portion 110 and along a part of the second absorbing portion 120. The third weakening line 160 is arranged for allowing an adjustment of the size of the first absorbing portion 110 and/or an apportionment of the first and second absorbing portions 110, 120 by tearing the hygiene article 100 along the third weakening line 160.

Figure 2:
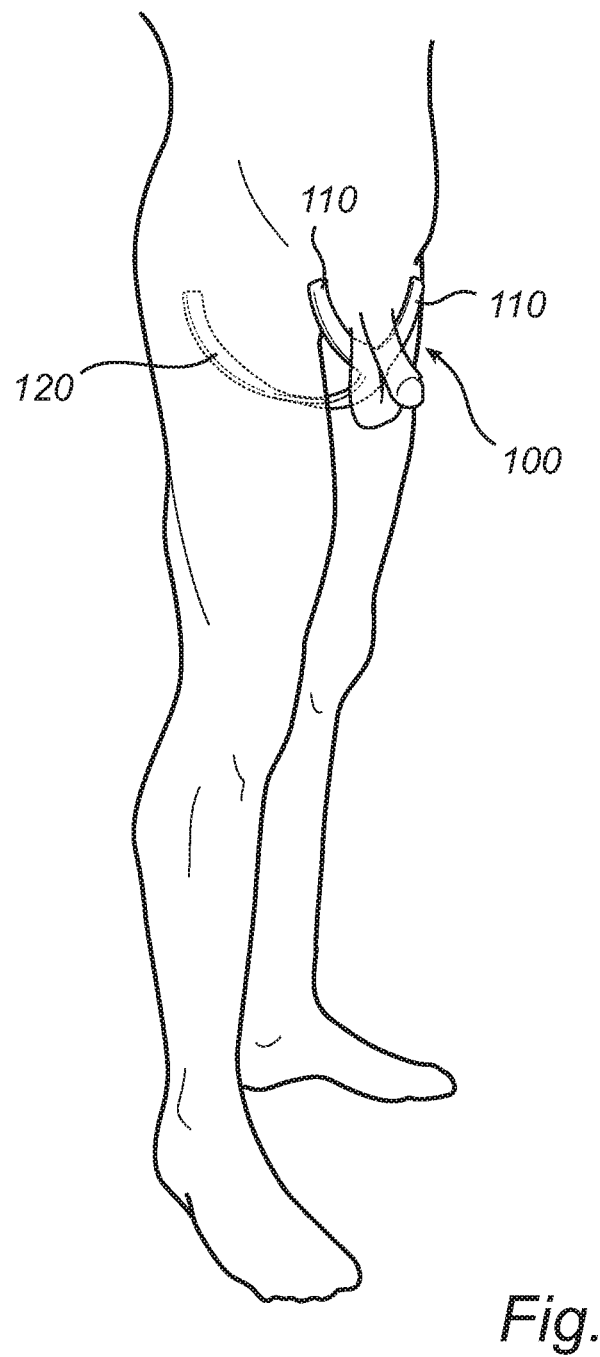
FIG. 2 is a schematic illustration of the hygiene article provided on a male user.

FIG. 2 is a schematic illustration of the hygiene article 100 provided on a male user, showing an exemplifying application of the hygiene article 100 to the crotch. Here, the first absorbing portion 110 of the hygiene article 100 receives the genitals of the male, wherein the second absorbing portion 120 of the hygiene article 100 is provided between the buttocks of the male.

Figure 3:
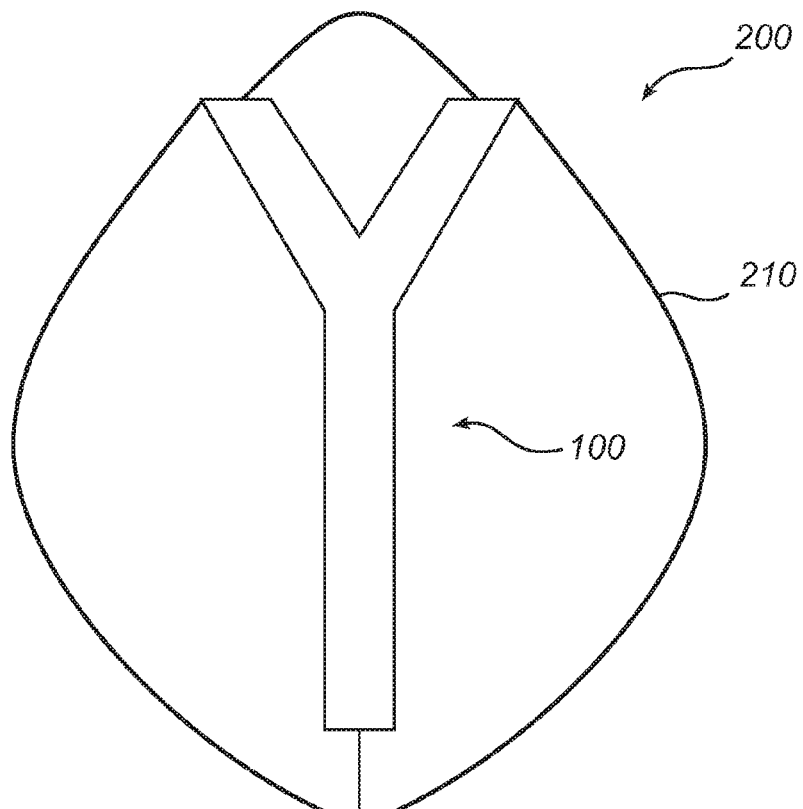
FIG. 3 is a schematic illustration of the underwear garment.

FIG. 3 is a schematic illustration of an underwear garment 200 comprising a one-piece hygiene article 100. A waistband 210, arranged to surround the torso of the male, is attached to the legs 111, 112 of the first absorbing portion 110 and to the second absorbing portion 120 so as to define openings for the legs of the male when putting on and wearing the underwear garment 200. It will be appreciated that the waistband 210 may comprise substantially any elastic material such that the underwear garment 200 may be conveniently and comfortably worn by the user.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

For example, the size/length apportionment of (the relation between) the first and the second absorbing portions 110, 120 of the hygiene article 100 may be different from that shown. For example, the "V"-shape of the first absorbing portion 110 may constitute a greater/smaller portion of the hygiene article 100 than that shown. Analogously, the "I"-shape of the second absorbing portion 120 may further constitute a greater/smaller portion of the hygiene article 100 than shown in FIG. 1. Furthermore, the first, second and third weakening lines 140, 150, 160 may be provided on other portions/parts/segments of the hygiene article 100 and/or be provided as more or fewer weakening lines 140, 150, 160 than those shown in FIG. 1.

The invention claimed is:

1. A one-piece hygiene article for use by a male to absorb moisture in the crotch region, said hygiene article comprising:
   an absorbent material;
   a first absorbing portion, having a V-shape for receiving the genitals of the male, and wherein legs of the V-shape of said first absorbing portion are arranged for being provided along the groin and on either side of the genitals of the male;
   a second absorbing portion, extending from a base of the V-shape of said first absorbing portion and having an elongated shape, wherein said second absorbing portion is arranged for being provided between the buttocks of the male;
   at least one weakening line arranged to allow an adjustment of a length of said hygiene article; and
   an adhesive material to adhere said hygiene article to the crotch of the male,
   wherein said at least one weakening line includes at least one first weakening line and wherein the at least one first weakening line extends from the base of the V-shape of said first absorbing portion and along at least a part of said second absorbing portion, said at least one first weakening line being arranged for allowing an adjustment of the size of said first absorbing portion by tearing apart said at least a part of said second absorbing portion along said at least one first weakening line.

2. The one-piece hygiene article of claim 1, wherein said adhesive material is provided at end parts of the legs of said first absorbing portion and at an end part of said second absorbing portion.

3. The one-piece hygiene article of claim 1, further comprising an attachment device to fasten said hygiene article to a piece of underwear.

4. The one-piece hygiene article of claim 1, wherein said at least one weakening line further includes at least one second weakening line and wherein at least one first segment of the legs of said first absorbing portion is provided with the at least one second weakening line, arranged to allow an adjustment of the length of the legs of said first absorbing portion by tearing off a portion of said at least one first segment at said at least one second weakening line.

5. The one-piece hygiene article of claim 4, wherein said at least one second weakening line includes at least one of a perforation line, a folding line, and a bending line.

6. The one-piece hygiene article of claim 4, wherein said at least one weakening line further includes at least one third weakening line and wherein at least one second segment of said second absorbing portion is provided with the at least one third weakening line, arranged to allow an adjustment of the length of said second absorbing portion by tearing off a portion of said at least one second segment at said at least one third weakening line.

7. The one-piece hygiene article of claim 6, wherein one or more of said at least one first, second and third weakening lines includes at least one of a perforation line, a folding line, and a bending line.

8. The one-piece hygiene article of claim 6, wherein said at least one third weakening line includes at least one of a perforation line, a folding line, and a bending line.

9. The one-piece hygiene article of claim 1, wherein said absorbent material is made of at least one of cellulose, cellulose fluff, wood fluff, and cotton.

10. The one-piece hygiene article of claim 1, further comprising at least one of a medicinal agent and deodorant.

11. The one-piece hygiene article of claim 1, wherein a length of said hygiene article is within 40-80 cm.

12. The one-piece hygiene article of claim 11, wherein a length of said hygiene article is within 50-70 cm.

13. The one-piece hygiene article of claim 1, wherein a width of said hygiene article is within 0.5-5 cm.

14. The one-piece hygiene article of claim 13, wherein a width of said hygiene article is within 1-3 cm.

15. The one-piece hygiene article of claim 1, wherein said at least one first weakening line includes at least one of a perforation line, a folding line, and a bending line.

16. An underwear garment, comprising:
    the one-piece hygiene article of claim 1; and
    an elastic waistband arranged to surround a torso of the male, wherein said elastic waistband is attached to the legs of said first absorbing portion and to said second absorbing portion so as to define openings for the legs of the male when putting on and wearing said underwear garment.

17. The underwear garment of claim 16, wherein the width of said hygiene article is within 0.5-2 cm.

18. The underwear garment of claim 16, wherein said at least one weakening line of the one-piece hygiene article further includes at least one second weakening line and wherein at least one first segment of the legs of said first absorbing portion is provided with the at least one second weakening line, arranged to allow an adjustment of the length of the legs of said first absorbing portion by tearing off a portion of said at least one first segment at said at least one second weakening line.

19. The underwear garment of claim 18, wherein said at least one weakening line of the one-piece hygiene article further includes at least one third weakening line and wherein at least one second segment of said second absorbing portion is provided with the at least one third weakening line, arranged to allow an adjustment of the length of said second absorbing portion by tearing off a portion of said at least one second segment at said at least one third weakening line.

20. The underwear garment of claim 19, wherein one or more of said at least one first, second and third weakening lines of the one-piece hygiene article includes at least one of a perforation line, a folding line, and a bending line.

* * * * *